US010939286B2

(12) United States Patent
Varanasi et al.

(10) Patent No.: US 10,939,286 B2
(45) Date of Patent: Mar. 2, 2021

(54) LINK STATUS-AWARE MEDICAL DEVICES AND GATEWAYS

(71) Applicant: PHILIPS HEALTHCARE INFORMATICS, INC., Cambridge, MA (US)

(72) Inventors: Nandini Varanasi, San Diego, CA (US); Eugene Dantsker, San Diego, CA (US)

(73) Assignee: Koninklijke Philips N.V., Eindhoven (NL)

( * ) Notice: Subject to any disclaimer, the term of this patent is extended or adjusted under 35 U.S.C. 154(b) by 0 days.

(21) Appl. No.: 16/532,429

(22) Filed: Aug. 5, 2019

(65) Prior Publication Data

US 2020/0045533 A1 Feb. 6, 2020

Related U.S. Application Data

(60) Provisional application No. 62/715,145, filed on Aug. 6, 2018.

(51) Int. Cl.
| | |
|---|---|
| *H04W 8/30* | (2009.01) |
| *H04L 1/16* | (2006.01) |
| *G06F 16/27* | (2019.01) |
| *G16H 80/00* | (2018.01) |

(52) U.S. Cl.
CPC .............. *H04W 8/30* (2013.01); *G06F 16/27* (2019.01); *G16H 80/00* (2018.01); *H04L 1/1642* (2013.01)

(58) Field of Classification Search
CPC ...................................................... H04W 4/80
See application file for complete search history.

(56) References Cited

U.S. PATENT DOCUMENTS

| | | | | |
|---|---|---|---|---|
| 10,200,842 | B1* | 2/2019 | Roy | H04L 67/12 |
| 10,219,242 | B2* | 2/2019 | Qiu | H04M 1/72527 |
| 10,360,368 | B2* | 7/2019 | Berman | G16H 40/63 |
| 2008/0304486 | A1* | 12/2008 | Graessley | H04L 65/608 |
| | | | | 370/392 |

(Continued)

OTHER PUBLICATIONS

Chris Geer: "TCP Series #3: Network Packet Loss, Retransmissions, and Dup Acks", Jun. 14, 2017, XP055623191, Retrieved from the Internet: URL:https://accedian.com/enterprises/bog/network-packet-loss-retransmissions-and-duplicate-acknoledgements/ [retrieved on Sep. 17, 2019] p. 2 par 2.

(Continued)

*Primary Examiner* — Wen W Huang

(57) ABSTRACT

Aspects of the subject matter described in this disclosure can be implemented in electronic medical devices, wireless gateway devices, and remote database systems in a network environment where wireless connections are made between at least an electronic device and a wireless gateway device, and between the wireless gateway device or an access point and a remote database system. The electronic medical device, the wireless gateway device, or the remote database system may be configured to identify a data communication loss based on at least a mismatch of a confirmation acknowledgement attribute between two or more nodes in the network environment. Upon identifying the data communication loss, a notification can be provided to an entity such as a user so that data communication can be restored.

20 Claims, 8 Drawing Sheets

(56) References Cited

U.S. PATENT DOCUMENTS

| | | | |
|---|---|---|---|
| 2014/0029411 A1* | 1/2014 | Nayak | G16H 40/67 |
| | | | 370/219 |
| 2014/0379368 A1* | 12/2014 | Kim | G06Q 50/22 |
| | | | 705/2 |
| 2015/0050888 A1 | 2/2015 | Baker et al. | |
| 2016/0035213 A1* | 2/2016 | Choi | H04L 63/107 |
| | | | 340/669 |
| 2016/0127559 A1* | 5/2016 | Baek | G06F 21/35 |
| | | | 455/417 |
| 2016/0315832 A1* | 10/2016 | Hu | H04L 25/20 |
| 2017/0280495 A1* | 9/2017 | Zhang | H04W 76/19 |
| 2018/0337866 A1* | 11/2018 | Jung | H04W 36/08 |

OTHER PUBLICATIONS

Anonymous: "networking—Does the sequence number of TCP packet headers wrap around?—Super User", Sep. 2, 2015, XP055623197, Retrieved from the Internet: URL: https://superuser.com/questions/966212/does-the-sequence-number-of-tcp-packet-headers-wrap-around [retrieved on Sep. 17, 2019] p. 3 last 2 par.

Anonymous: "Transmission Control Protocol—Wikipedia", Jul. 31, 2018, XP055623931, Retrieved from the Internet: URL: https://de.wikipedia.org/w/index.php?titie=Transmission_Control_Protocol&oldid=179596123 [retrieved on Sep. 19, 2019] p. 4 penultimate par-p. 5 par 3.

Anonymous: "RFC 1323—TCP Extensions for High Performance", May 31, 1992, XP055623941, Retrieved from the Internet: URL: hitps://tools.ietf.org/html/rfc1323 [retrieved on Sep. 19, 2019] p. 17 sections 4.1 and 4.2.

International Application No. PCT/US2019/045213, "International Search Report and Written Opinion" dated Nov. 14, 2019, 13 pages.

* cited by examiner

LINK STATUS-AWARE MEDICAL DEVICES AND GATEWAYS

CROSS-REFERENCES TO RELATED APPLICATIONS

This application is a non-provisional of and claims the benefit of and priority to U.S. Provisional Application No. 62/715,145, filed Aug. 6, 2018, entitled "LINK STATUS-AWARE MEDICAL DEVICES AND GATEWAYS," the content of which is herein incorporated by reference in its entirety for all purposes.

BACKGROUND

Information sharing across electronic devices is becoming more common with device-to-device wireless communication. Electronic devices can be paired together so that the electronic devices are associated with one another, and the electronic devices can share information by wirelessly transferring data.

Some such electronic devices may include personal medical devices such as activity trackers, wearable patches, continuous glucose sensors, and other medical devices that sense and communicate patient data. Some such electronic devices may also include gateway wireless devices such as smartphones, smart watch, tablet, laptop, or dedicated wireless communication hubs. Personal medical devices and gateway wireless devices may be paired so that data can be wirelessly transferred, and the gateway wireless devices may upload the data to a server. However, the transfer of data may be disrupted as a result of one or more broken wireless links, and patients, health care providers, payers, stakeholders, or users may not be aware of the one or more broken wireless links. Valuable data may be lost that can lead to significant health and economic impact.

BRIEF SUMMARY

This disclosure relates generally to wireless communication of personal medical data, and more particularly, to identifying broken wireless links in wireless communication of personal medical data.

The systems, methods and devices of this disclosure each have several aspects, no single one of which is solely responsible for the desirable attributes disclosed herein.

One aspect of the subject matter described in this disclosure can be implemented in an electronic device. The electronic device includes a radio-frequency (RF) communications circuitry, one or more sensors configured to measure and/or collect biometric data, and a control system coupled to the RF communications circuitry. The control system is configured to transmit the biometric data from the electronic device to the wireless gateway device in a first wireless connection, where the wireless gateway device is configured to upload the biometric data to a remote database system. The control system is further configured to identify a data communication loss based at least on a mismatch of a confirmation acknowledgement attribute between two or more of the electronic device, the wireless gateway device, or the remote database system. The control system may then provide a notification indicating the data communication loss.

In some implementations, the control system is configured to identify the data communication loss while a wireless connection is available and active between the remote database system and the wireless gateway device. In some implementations, the control system is configured to identify the data communication loss while the electronic device and the wireless gateway device are wirelessly paired. In some implementations, the wireless gateway device is configured to upload the biometric data to the remote database system in a second wireless connection, the second wireless connection provided over a wireless local area network (WLAN) and the first wireless connection provided over a personal area network (PAN). In some implementations, the electronic device further includes a feedback component coupled to the control system, where the control system is configured to provide the notification through the feedback component by a visual notification, audible notification, haptic notification, or combinations thereof. In some implementations, the wireless gateway device comprises an access point, wireless communications hub, mobile phone, smartphone, tablet, PDA, laptop computer, desktop computer, smart watch, or smart clothing. In some implementations, the confirmation acknowledgement attribute includes a sequence identification number. In some implementations, the confirmation acknowledgement attribute includes a timestamp. In some implementations, the confirmation acknowledgement attribute includes a maximum segment size.

Another aspect of the subject matter described in this disclosure can be implemented in a gateway device including a radio-frequency (RF) communications circuitry and a control system coupled to the RF communications circuitry. The control system is configured to: connect the gateway device wirelessly with an electronic device configured to measure and/or collect biometric data, receive the biometric data from the electronic device, transmit the biometric data to one or more access points or a remote database system, identify a data communication loss based at least on a mismatch of a confirmation acknowledgement attribute between two or more of: the electronic device, the gateway device, the one or more access points, or the remote database system, and provide a notification indicating the data communication loss.

In some implementations, the confirmation acknowledgement attribute is selected from a sequence identification number, a timestamp, or a maximum segment size. In some implementations, the control system is configured to provide the notification indicating the data communication loss via email, text message, multimedia message, or mobile app message.

Another aspect of the subject matter described in this disclosure can be implemented in a database system including a radio-frequency (RF) communications circuitry, and a control system coupled to the RF communications circuitry. The control system is configured to connect the database system wirelessly with a gateway device, where the gateway device is configured to receive biometric data measured and/or collected by an electronic device. The control system is further configured to receive the biometric data from the gateway device, and identify a data communication loss. The data communication loss may be identified based on a mismatch of a confirmation acknowledgement attribute between two or more of the electronic device, the gateway device, one or more access points, or the database system. The control system may then provide a notification indicating the data communication loss.

In some implementations, the confirmation acknowledgement attribute is selected from a sequence identification number, a timestamp, or a maximum segment size. In some implementations, the control system is configured to provide the notification indicating the data communication loss via email, text message, multimedia message, or mobile app message.

Another aspect of the subject matter described in this disclosure can be implemented in a method of identifying a data communication loss in a network. The method includes establishing one or more wireless connections in the network for transmitting data from an electronic device to a remote database system via one or more gateway devices, identifying a data communication loss based at least on a mismatch of a confirmation acknowledgement attribute between two or more of: the electronic device, the remote database system, or the one or more gateway devices, and providing a notification indicating the data communication loss.

In some implementations, the confirmation acknowledgement attribute is selected from a sequence identification number, a timestamp, or a maximum segment size.

Details of one or more implementations of the subject matter described in this disclosure are set forth in the accompanying drawings and the description below. Other features, aspects, and advantages will become apparent from the description, the drawings and the claims. Note that the relative dimensions of the following figures may not be drawn to scale.

BRIEF DESCRIPTION OF THE DRAWINGS

Like reference numbers and designations in the various drawings indicate like elements.

DETAILED DESCRIPTION

Figure 1:
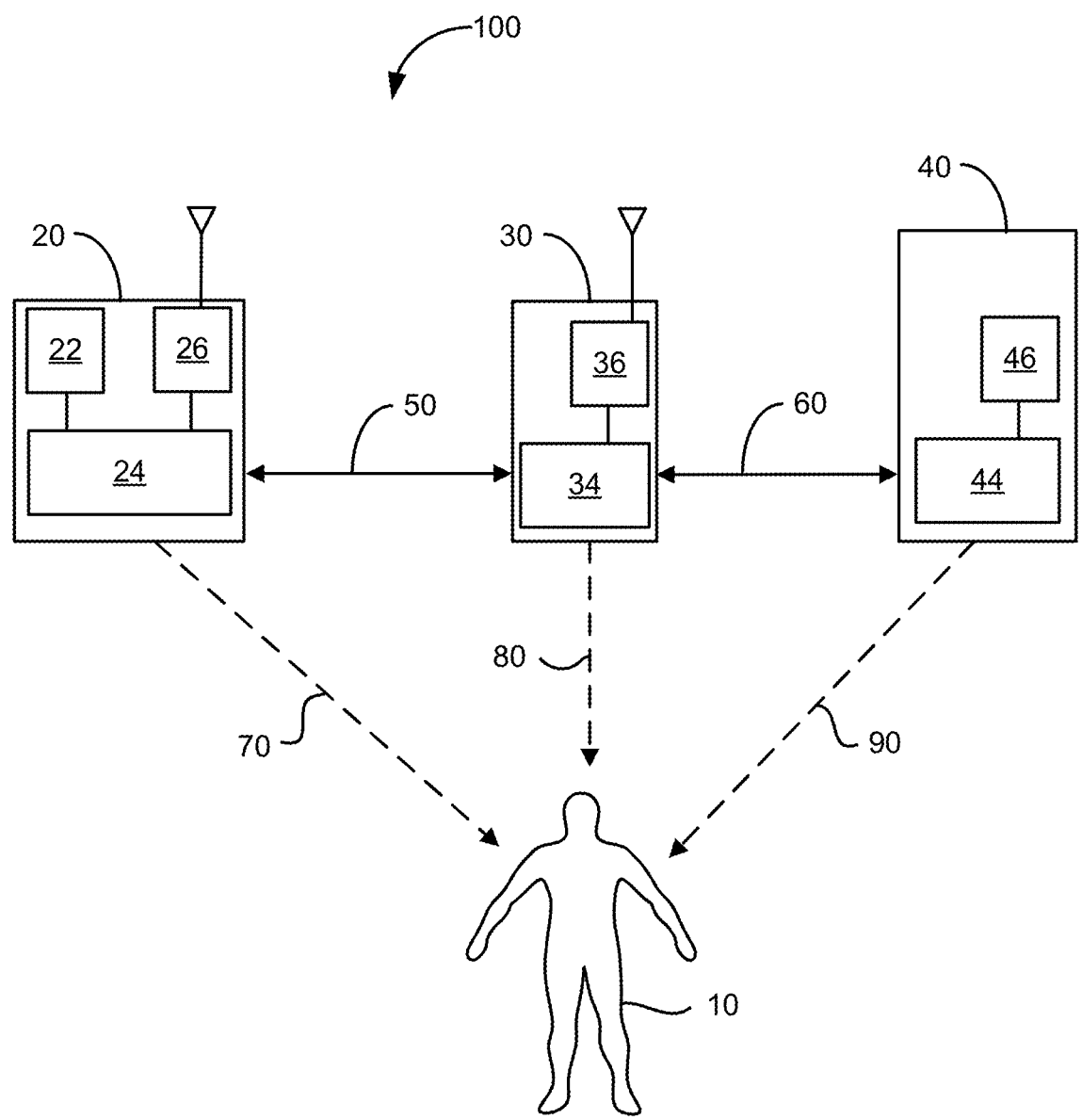
FIG. 1 illustrates a schematic diagram illustrating wireless links and communication pathways in an example network environment including an electronic medical device, a wireless gateway device, and a remote database system according to some implementations.

The following description is directed to certain implementations for the purposes of describing various aspects of this disclosure. However, a person having ordinary skill in the art will readily recognize that the teachings herein can be applied in a multitude of different ways. Various embodiments will be described in detail with reference to the accompanying drawings. References made to particular examples and implementations are for illustrative purposes, and are not intended to limit the scope of the claims.

The described implementations may be implemented in any device, apparatus, or system that is configured to communicate with another device, apparatus, or system. In addition, it is contemplated that the described implementations may be included in or associated with a variety of electronic devices such as, but not limited to: mobile telephones, multimedia Internet enabled cellular telephones, mobile television receivers, wireless devices, smartphones, smart cards, wearable devices such as bracelets, armbands, wristbands, rings, headbands, patches, belts, etc., Bluetooth® devices, personal data assistants (PDAs), wireless electronic mail receivers, hand-held or portable computers, netbooks, notebooks, smartbooks, tablets, printers, copiers, scanners, facsimile devices, global navigation satellite system (GNSS) receivers/navigators, cameras, digital media players (such as MP3 players), camcorders, game consoles, wrist watches, clocks, calculators, television monitors, flat panel displays, implantable medical devices, interrogator medical devices, electronic reading devices (e.g., e-readers), mobile health devices, medical devices, fitness trackers, activity trackers, wearable patches, computer monitors, auto displays, cockpit controls and/or displays, steering wheels, camera view displays, electronic photographs, electronic billboards or signs, projectors, architectural structures, microwaves, refrigerators, stereo systems, cassette recorders or players, DVD players, CD players, VCRs, radios, portable memory chips, washers, dryers, washer/dryers, parking meters, etc. By way of example, the described implementations may be implemented in an electronic medical device. For example, the described implementations may be implemented in a fitness or activity tracker, wearable patch, continuous glucose sensor, or other electronic medical device that senses and communicates patient data. Some of the described implementations may be implemented in a wireless gateway device. For example, the described implementations may be implemented in an access point, a wireless communications hub, a mobile phone, a tablet, a PDA, a laptop computer, a desktop computer, a smartphone, a smart watch, or smart clothing. Some of the described implementations may be implemented in a database system such as a cloud-based server. Nonetheless, the teachings are not intended to be limited to the implementations depicted solely in the Figures, but instead have wide applicability as will be readily apparent to one having ordinary skill in the art.

This disclosure relates generally to devices, systems, and methods regarding identification and notification of data communication loss in a network including electronic medical devices, wireless gateway devices, and servers. An electronic medical device may be configured to measure and/or collect biometric data of a user. A wireless gateway device may be configured to wirelessly receive the biometric data from the electronic medical device and transmit the biometric data to an access point or server. One or more wireless connections may be established between the electronic medical device and the wireless gateway device, the wireless gateway device and the access point, the wireless gateway device and the server, and/or the electronic medical device and server. A data communication loss, such as a packet loss or message loss, is identified based at least on a mismatch of a confirmation acknowledgement attribute between two or more of: the electronic medical device, the wireless gateway device, or the server. A notification is provided to the electronic medical device or wireless gateway device indicating the identified data communication loss.

Particular implementations of the subject matter described in this disclosure can be implemented to realize one or more of the following potential advantages. Reliable identification and notification of a data communication loss in a network enables more efficient restoration of broken wireless connections. Loss of valuable data including medical, wellness, and fitness data of a user is averted or at least minimized. Preservation of such data improves user satisfaction, facilitates accurate monitoring of user data, and ensures the integrity and continuity of the user data. Stakeholders and health care providers may provide improved health care to the user with the accurate user data, and payers or other entities may financially reward the user with the accurate user data.

FIG. 1 shows a schematic diagram illustrating wireless links and communication pathways in an example network environment 100 including an electronic medical device 20, a wireless gateway device 30, and a remote database system 40 according to some implementations. An electronic device 20 may be any electronic medical device with one or more sensors 22. The electronic device 20 may serve as a biomedical or biometric device that is capable of sensing and communicating user data. As used herein, the electronic device 20 may be used interchangeably with "electronic medical device," "electronic sensor device," "sensor device," "biomedical device," "biometric device," "biometric tracking device," "personal health monitoring device," "portable monitoring device," "biometric monitoring device," and the like. Examples of the electronic device 20 include activity trackers, fitness trackers, wearable patches, blood pressure sensors, continuous glucose sensors, and other medical devices that sense user data. In some implementations, the electronic device 20 may be wearable or otherwise attachable to the user's body.

The one or more sensors 22 of the electronic device 20 may be used to sense or measure detectable physical phenomena or quantities. The one or more sensors 22 may be used to take readings or measurements of a user's body. The one or more sensors 22 may measure and/or collect biometric data regarding the user. Biometric data may include physiological characteristics of the user, including but not limited to heart rate, perspiration levels, blood pressure, blood glucose, body temperature, weight, respiration rate, blood oxygen levels, skin conduction, brain activity, hydration levels, etc. Biometric data may also include activity data of the user, including but not limited to step count, calories burned, floors climbed/descended, swim lap count, ambulatory speed and/or distance traveled, bicycle distance and/or speed, sleep duration, sleep quality, nutritional intake from food, etc.

The biometric data measured and/or collected by the one or more sensors 22 may be processed by a control system 24. The electronic device 20 is configured to wirelessly transmit the biometric data obtained by the one or more sensors 22.

The electronic device 20 includes the control system 24 and a radio-frequency (RF) communications circuitry 26 coupled to the control system 24. In some implementations, the RF communications circuitry 26 may include one or more of a receiver, a transmitter, or a two-way transceiver. The RF communications circuitry 26 may operate in one or more frequency bands depending on the supported type of communications.

The network environment 100 may further include a wireless gateway device 30 configured to receive the biometric data from the electronic device 20. The wireless gateway device 30 may serve to transfer or upload the biometric data to a remote database system 40 such as a cloud-based database system or server. In some implementations, the wireless gateway device 30 may transfer or upload the biometric data to the remote database system 40 via one or more access points (not shown). In some implementations, wireless gateway device 30 may transfer or upload the biometric data to the remote database system 40 directly.

In some implementations, the wireless gateway device 30 is an access point, wireless communications hub, or other device with wireless communications capability. The wireless gateway device 30 may be able to communicate data wirelessly by serving as an Internet-accessible data source and/or by serving to relay the data to other external devices. The wireless gateway device 30 can be a wireless communications hub, such as a 2Net hub, that facilitates end-to-end connectivity from the electronic device 20 to the remote database system 40. In some implementations, the wireless gateway device 30 can include but is not limited to a mobile phone, smartphone, tablet, PDA, laptop computer, desktop computer, smart watch, smart clothing, or other device with wireless communication capability. For example, the wireless gateway device 30 may include a display for displaying the biometric data.

The wireless gateway device 30 can include a second control system 34 and a second RF communications circuitry 36 coupled to the second control system 34. In some implementations, the second RF communications circuitry 36 may include one or more of a receiver, a transmitter, or a two-way transceiver. The second RF communications circuitry 36 may operate in one or more frequency bands depending on the supported type of communications. As shown in FIG. 1, the electronic device 20 may wirelessly communicate with the wireless gateway device 30 via a first wireless connection 50. The first wireless connection 50 facilitates transfer of the biometric data from the electronic device 20 to the wireless gateway device 30. The first wireless connection 50 between the electronic device 20 and the wireless gateway device 30 may be bidirectional and may be through a wireless communication interface and protocol such as a personal area network (PAN), near-field communication (NFC), or wireless local area network (WLAN). For example, the first wireless connection 50 may be provided through a Bluetooth® protocol. In some implementations, the first wireless connection 50 may be established between the electronic device 20 and the wireless gateway device 30 by device pairing.

The network environment 100 may further include the remote database system 40 configured to receive the biometric data from the wireless gateway device 30 directly or via one or more access points. The remote database system 40 may be operated by an external service (e.g., a cloud server) for storing and/or processing the biometric data. In some implementations, the remote database system 40 is accessible to the user or other entities through the Internet.

The remote database system 40 can include a third control system 44 and a third RF communications circuitry 46 coupled to the third control system 44. In some implementations, the third RF communications circuitry 46 may include one or more of a receiver, a transmitter, or a two-way transceiver. The third RF communications circuitry 46 may operate in one or more frequency bands depending on the supported type of communications. As shown in FIG. 1, the wireless gateway device 30 may wirelessly communicate with the remote database system 40 via a second wireless connection 60. The second wireless connection 60 facilitates transfer of the biometric data from the wireless gateway device 30 to the remote database system 40. The second wireless connection 60 between the wireless gateway device 30 and the remote database system 40 may be bidirectional and may be through a wireless communication interface and protocol such as WLAN or a wireless wide area network (WWAN). For example, the second wireless connection may be provided through a Wi-Fi® protocol.

Though not shown in FIG. 1, additional wireless connections may exist from the wireless gateway device 30 to the remote database system 40 with one or more access points or secondary devices. Each of the electronic device 20, the wireless gateway device 30, the remote database system 40, and the one or more access points or secondary devices may serve as nodes in the network environment 100. The network environment 100 may have any number of nodes facilitating transfer of data between nodes. The nodes may be connected by wireless connections/links that can provide end-to-end connectivity from an edge client device to a server.

It is possible that any one of the wireless connections/links in the network environment 100 can be broken or disrupted. Wireless transmissions between nodes may be broken or disrupted, including disruptions in the first wireless connection 50 or the second wireless connection 60. There may be multiple points of failure in transmission of data. To illustrate some examples of how a wireless connection/link can be broken or disrupted, a sequence in a packet may be invalid, a mismatch in timestamps may occur, a connection error may occur, a server may drop a message, or a mobile phone may drop a message. Specific messaging loss can occur even while connectivity between nodes is active and available. Any of these points of failure in the network environment 100 may result in data being lost or compromised. Should a consumer-grade wireless connection/link fail, a user is typically actively involved and can readily restore the connection without significant detrimental effect. However, should a medical-grade wireless connection/link fail, any interested entity in the medical data such as a user, healthcare provider, stakeholder, or payer may not be aware of the medical data being lost or compromised. Among a number of possible negative consequences, this can have significant detrimental effect on patient well-being.

Aspects of the present disclosure provide identification of data communication loss based on a mismatch of a confirmation acknowledgement attribute between two or more nodes in a network environment 100, and providing a notification of the identified data communication loss. In some implementations, the confirmation acknowledgement attribute may be a sequence identification number, a timestamp, or a maximum segment size. The notification may originate from the electronic device 20, the wireless gateway device 30, or the remote database system 40 to alert an entity 10 of the identified data communication loss. Examples of the entity 10 can include a user of the electronic device 20, health care providers, payers, and stakeholders. Upon being alerted, the entity 10 can restore any broken wireless connections/links between nodes in the network environment 100.

Providing the notification to the entity 10 can occur in one or more ways. In some implementations, a first notification 70 may originate from the electronic device 20 indicating a data communication loss. The electronic device 20 may provide the first notification 70 through a feedback mechanism in the electronic device 20. For example, a feedback component may be coupled to the control system 24 in the electronic device 20, where the control system 24 is configured to provide the first notification 70 through the feedback component by a visual notification, audible notification, haptic notification, or combinations thereof.

In some implementations, a second notification 80 may originate from the wireless gateway device 30 indicating a data communication loss. The wireless gateway device 30 may provide the second notification 80 through a feedback mechanism in the wireless gateway device 30 or through an accessible application layer to the entity 10. By way of an example, the wireless gateway device 30 may deliver the second notification 80 using a display for visual feedback, a speaker for audio feedback, and/or a vibration motor for haptic feedback. By way of another example, the wireless gateway device 30 may deliver the second notification 80 using alternate communication channels not broken or disrupted, which may include email, text message, multimedia message, or mobile app message.

In some implementations, a third notification 90 may originate from the remote database system 40 indicating a data communication loss. The remote database system 40 may provide the third notification 90 through an accessible application layer to the entity 10. By way of an example, the remote database system 40 may deliver the third notification 90 using alternate communication channels not broken or disrupted, which may include email, text message, multimedia message, or mobile app message.

Figure 2A:
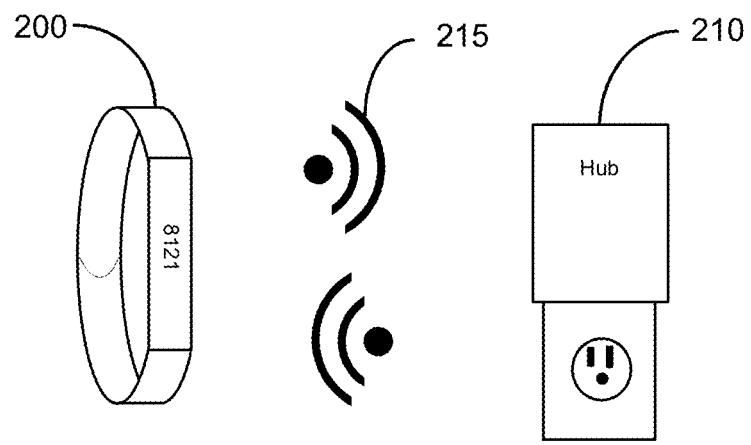
FIG. 2A illustrates a schematic illustration of an example wireless connection between a personal medical device and a wireless communications hub according to some implementations.
Figure 2B:
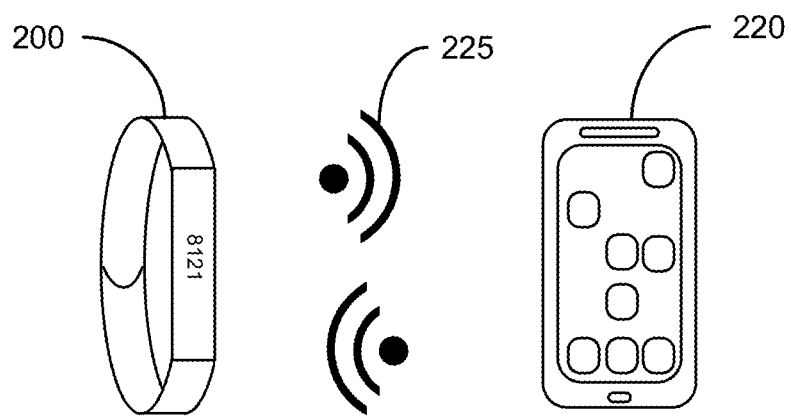
FIG. 2B illustrates a schematic illustration of an example wireless connection between a personal medical device and a mobile device according to some implementations.

FIGS. 2A and 2B illustrate two different ways that data can be wirelessly transmitted so that the data can ultimately reach a remote database system such as a cloud-based server. FIG. 2A shows a schematic illustration of an example wireless connection between a personal medical device 200 and a wireless communications hub 210 according to some implementations. In FIG. 2A, a personal medical device 200 such as a fitness tracker can transmit data to a wireless communications hub 210 such as a 2Net hub. Radio transmissions 215 can be transmitted between the personal medical device 200 and the wireless communications hub 210 using compatible wireless protocols such as Bluetooth®, Wi-Fi®, 2.4 GHz ANT, or USB. FIG. 2B shows a schematic illustration of an example wireless connection between a personal medical device 200 and a mobile device 220 according to some implementations. In FIG. 2B, a personal medical device 200 such as a fitness tracker can transmit data to a mobile device 220 such as a smartphone, where the smartphone may be configured to upload the data to the remote database system via a mobile app. Radio transmissions 225 can be transmitted between the personal medical device 200 and the mobile device 220 using compatible wireless protocols such as Bluetooth® or Wi-Fi®.

Figure 3:
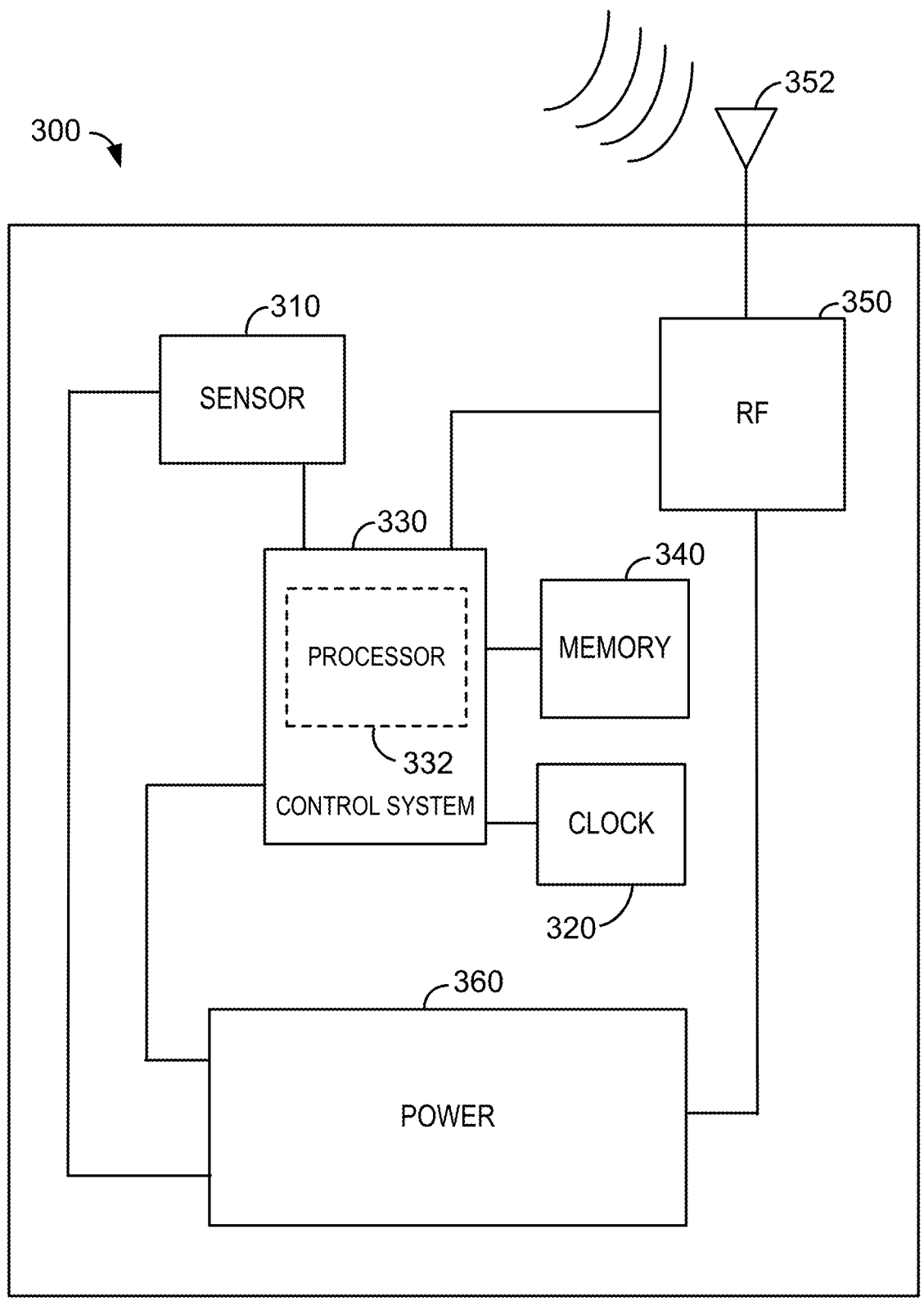
FIG. 3 illustrates a block diagram representation of components of an example electronic medical device according to some implementations.

FIG. 3 illustrates a block diagram representation of components of an example electronic medical device according to some implementations. In some implementations, the electronic medical device 300 may be a biomedical device or biometric device such as a fitness tracker. As with other implementations disclosed herein, the number of elements and types of elements shown in FIG. 3 are merely by way of example. Other implementations may have more, fewer, or different elements. In the implementation in FIG. 3, the electronic device 300 includes a sensor 310, a clock 320, a control system 330, a memory 340, a wireless communications component 350 coupled to an antenna 352, and a power supply 360.

In some implementations, the electronic device 300 includes one or more sensors 310. The one or more sensors 310 may be configured to measure and/or collect biometric data. Non-limiting examples of sensors 310 may include temperature sensors, pulse sensors, electric field sensors, moisture sensors, liquid flow sensors, magnetic sensors, piezoelectric sensors, pressure sensors, optical sensors, chemical sensors (e.g., blood glucose sensors), and other biomedical sensors. In some implementations, the biometric data may be accessed by the control system 330 and transmitted to an external device.

The electronic device 300 can include a clock 320 internal to the electronic device 300. In some implementations, the clock 320 may be able to record timestamps data obtained by the one or more sensors 310 as well as record timestamps of packets or messages wirelessly received or transmitted by the wireless communications component 350. In some implementations, the clock 320 may be set to a specified time zone. However, the timestamps of packets or messages wirelessly received or transmitted may be set to a reference time zone (e.g., Greenwich Mean Time (GWT)). That way, the timestamps of packets or messages may be unified regardless of different time zones in which the electronic device 300 and secondary devices may reside.

Figure 4:
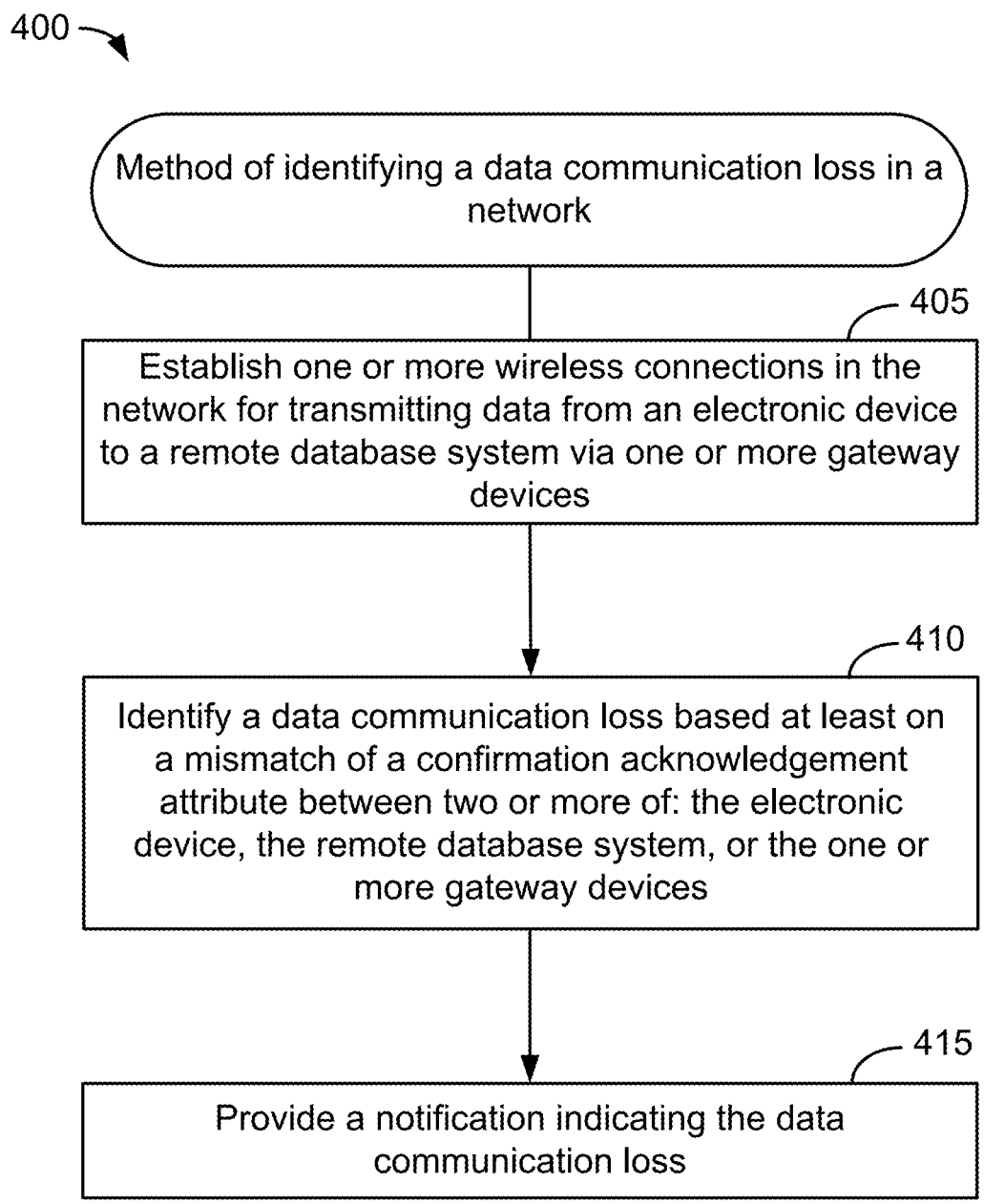
FIG. 4 illustrates a flow diagram illustrating an example process identifying a data communication loss in a network according to some implementations.

The electronic device 300 can include a control system 330. The control system 330 may include at least one of a general purpose single- or multi-chip processor, a digital signal processor (DSP), an application specific integrated circuit (ASIC), a field programmable gate array (FPGA) or other programmable logic device, discrete gate or transistor logic, or discrete hardware components. In some implementations, the control system 330 may include a processor 332. The control system 330 may be capable of performing some or all of the methods described herein. According to some examples, the control system 330 may be capable of performing a method described in a process 400, which is shown in FIG. 4. In some implementations, the control system 330 may be capable of controlling one or more components of the electronic device 300. For example, the control system 330 may be capable of controlling the one or more sensors 310. The control system 330 may be capable of controlling the wireless communications component 350.

In some implementations, the control system 330 may be capable of controlling the electronic device 300 according to instructions (e.g., software) stored on one or more non-transitory computer-readable media. Such non-transitory media may include the memory 340 of the electronic device 300. The memory 340 can store processor-executable instructions and/or outputs from the one or more sensors 310. In some implementations, the memory 340 may be a volatile memory, non-volatile memory (e.g., flash memory), or a combination thereof. In some implementations, the memory 340 may include internal memory included in the control system 330, memory external to the control system 330, or a combination thereof. The memory 340 may be coupled to the control system 330. In some implementations, the memory 340 may store information or instructions related to identification of data communication loss based at least on a mismatch of a confirmation acknowledgement attribute between two or more nodes in a network environment, and providing a notification indicating the identified data communication loss.

The electronic device 300 can include a wireless communications component 350 coupled to an antenna 352. The control system 330 may be coupled to the wireless communications component 350 to control the operations of the wireless communications component 350. In some implementations, the wireless communications component 350 may include one or more of a receiver, a transmitter, and a two-way transceiver. The wireless communications component 350 may wirelessly transmit the biometric data obtained from the one or more sensors 310 through a wireless communication interface and protocol such as Bluetooth® or Wi-Fi®.

In some implementations, one or more of the sensor 310, the clock 320, the control system 330, the memory 340, the wireless communications component 350, and any other electronic components of the electronic device 300 may be powered by the power supply 360. In some implementations, the power supply 360 may be a battery.

FIG. 4 illustrates a flow diagram illustrating an example process 400 identifying a data communication loss in a network according to some implementations. The process 400 may be performed in a different order or with different, fewer, or additional operations. Process 400 may be performed by one or more components (e.g., electronic medical device 20, wireless gateway device 30, or remote database system 40) described with respect to FIG. 1.

At block 405 of the process 400, one or more wireless connections are established in a network for transmitting data from an electronic device to a remote database system via one or more gateway devices. The electronic device may be an electronic medical device, biomedical device, or biometric device configured to measure and/or collect biometric data. The biometric data may include personal medical data, wellness data, or fitness data. The biometric data may be wirelessly transferred to the one or more gateway devices, and the one or more gateway devices may upload the biometric data to the remote database system. The one or more gateway devices may include one or more access points, wireless communications hubs, mobile phones, smartphones, tablets, PDAs, laptop computers, desktop computers, smart watches, or other devices with wireless communication capabilities.

Figure 5:
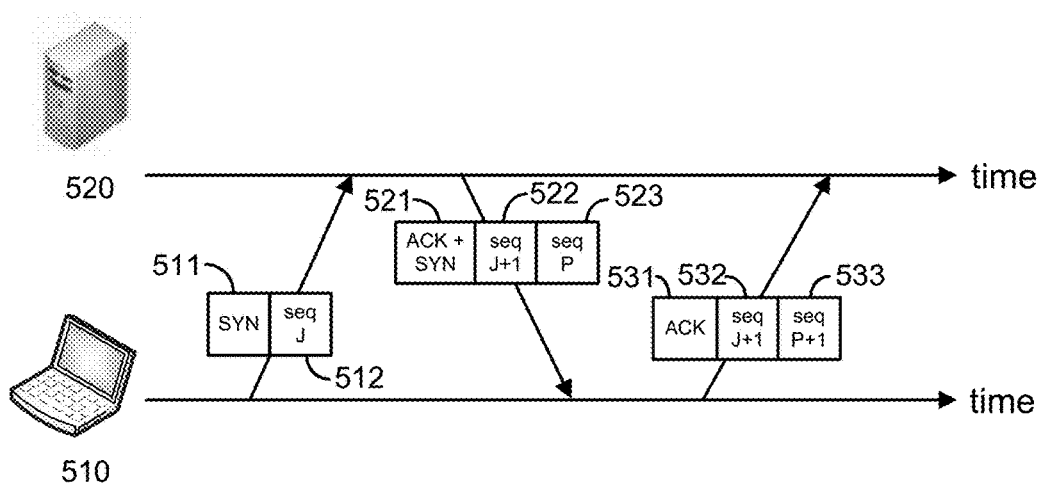
FIG. 5 illustrates a schematic diagram of an example three-way handshake for synchronization of sequence identification numbers between a source node and a destination node according to some implementations.

A wireless connection between the electronic device and at least one of the one or more gateway devices may be established by advertising and acknowledgement in a handshaking process. In some implementations, the electronic device and a gateway device are wirelessly paired upon completion of the handshaking process so that data may be transferred between the devices. For example, establishing the wireless connection between the electronic device and the gateway device can be accomplished by a three-way handshake. The electronic device sends a synchronize (SYN) message to the gateway device, the gateway device receives the SYN message and sends an acknowledgement (ACK) message that also contains the SYN message from the electronic device, and the electronic device receives the SYN-ACK message and sends an acknowledgement (ACK) message to the gateway device. An example of a three-way handshake is shown in FIG. 5, which is discussed in more detail below.

A wireless connection between the remote database system and at least one of the one or more gateway devices may also be established by a handshaking process such as a three-way handshaking process. The remote database system and a gateway device may be wirelessly connected by a TCP/IP connection. In some implementations, the wireless communication between the electronic device and at least one of the gateway devices may occur through a data link layer (Layer 2, e.g., Bluetooth®), and the wireless communication between at least one of the gateway devices and the remote database system may occur through a transport layer (Layer 4, e.g., TCP/IP). Thus, data transfer between nodes in the network may occur across different wireless communication interfaces and protocols. Such mismatches in wireless communication interfaces and protocols may result in more vulnerabilities for wireless communication failures in the network.

Additional wireless connections may be established between gateway devices. This adds more wireless connections in the network, which can add more vulnerabilities for wireless communication failures. For example, a wireless connection may be established between a mobile device and a wireless communications hub or an access point, or between a wireless communications hub and an access point.

At block 410 of the process 400, a data communication loss is identified based at least one a mismatch of a confirmation acknowledgement attribute between two or more of: the electronic device, the remote database system, or the one or more gateway devices. The data communication loss can be indicative of a broken or disrupted wireless communication between nodes in the network. In some implementations, the data communication loss can be a message loss or packet loss while connectivity is active and available. Even when a wireless connection is established (e.g., pairing) and remains active between the electronic device and a gateway device, or even when a wireless connection is established (e.g., TCP/IP connection) and remains active between the remote database system and a gateway device, data may be lost in wireless communication because of a message or packet loss. For example, a data communication loss can include a message being dropped at the remote database system or at one of the gateway devices. Accordingly, in some implementations, data communication loss can be identified while the electronic device and a gateway device are wirelessly paired. In some implementations, data communication loss can be identified while a wireless connection is available and active between the remote database system and a gateway device.

A mismatch in a confirmation acknowledgement attribute can be indicative of a packet or message loss. Each packet in a data communication can include at least a header and a payload. The payload may include the message and the header may include one or more flags such as a sequence identification number. In some implementations, the one or more flags may include a maximum segment size (MSS).

A packet may be transmitted from a source node and received by a destination node. It will be understood that nodes in a network, including the electronic device, the remote database system, and the one or more gateway devices, may serve as source nodes and/or destination nodes depending on whether it is transmitting or receiving packet transmissions. The packet transmitted from the source node may include a header and a payload having one or more attributes. When the destination node receives the packet, the destination node may respond with a confirmation acknowledgement having an ACK flag to acknowledge receipt of the packet. An attribute of the confirmation acknowledgement from the destination node may not match the one or more attributes of the packet received from the source node. This may be referred to as a mismatch in a confirmation acknowledgement attribute between nodes. In some implementations, the confirmation acknowledgement attribute includes a sequence identification number. In one mechanism, a sequence of the sequence identification numbers may be invalid. In another mechanism, selective acknowledgement of sequence identification numbers may filter data by removing duplicate transmissions. In some implementations, the confirmation acknowledgement attribute includes a timestamp. In some implementations, the confirmation acknowledgement attribute includes a maximum segment size. Accordingly, the confirmation acknowledgement attribute may be selected from a group consisting of: a sequence identification number, a timestamp, and a maximum segment size. Each of the foregoing confirmation acknowledgement attributes is discussed in further detail below with respect to FIGS. 5-8.

A packet loss or message loss may be identified where there is a mismatch in sequence identification numbers between at least a source node and a destination node. The source node may include the electronic device and or at least one of the one or more gateway devices. The destination node may include at least one of the one or more gateway devices or the remote database system. A sequence identification number may be set with SYN, SYN-ACK, or ACK flag of a packet header. A mismatch in the sequence identification number may occur where an initial sequence identification number transmitted with a SYN flag does not match with a sequence identification number transmitted with an ACK or SYN-ACK flag. The mismatch in the sequence identification number may be identified by any of the nodes in the network, including the electronic device, the remote database system, and the one or more gateway devices.

FIG. 5 illustrates a schematic diagram of an example three-way handshake for synchronization of sequence identification numbers between a source node 510 and a destination node 520 according to some implementations. A source node 510 (e.g., client device) sends a first packet having a SYN message to a destination node 520. The first packet includes a SYN flag 511 set to an initial sequence identification number 512. In some implementations, the initial sequence identification number 512 may be randomly generated, which is set to "J" in FIG. 5. The SYN message is received by the destination node 520 and sends a confirmation acknowledgement with an ACK message in a second packet to the source node 510. The second packet includes a SYN-ACK flag 521 set to its own sequence identification number 523, which can be "P" in FIG. 5, and also acknowledges the initial sequence identification number 512 with a return sequence identification number 522, which can be "J+1" in FIG. 5. The ACK message is received by the source node 510 and sends a confirmation acknowledgement with its own ACK message in a third packet to the destination node 520. The third packet includes an ACK flag 531 set to acknowledge the return sequence identification number 522 with an acknowledgement sequence identification number 532, which can be "J+1" in FIG. 5, and also acknowledges the sequence identification number 523 with a return sequence identification number 533, which can be "P+1" in FIG. 5. The three-way handshake illustrates synchronization of sequence identification numbers between a source node 510 and a destination node 520. Where an invalid sequence identification number is detected, this can be indicative of a packet loss or message loss in a wireless connection. Any one of the electronic device, the one or more gateway devices, and the remote database system may be configured to synchronize sequence identification numbers in confirmation acknowledgement and detect receipt of an invalid sequence identification number.

Returning to the process 400 of FIG. 4, a packet loss or message loss may be identified where there is a mismatch in maximum segment size between at least a source node and a destination node. The maximum segment size specifies the largest amount of data, measured in bytes, which can be provided in a payload of a single packet. In other words, the maximum segment size is the largest amount of useful information that can be sent in a single packet. The maximum segment size does not count the standard sizes of TCP and IP headers. The maximum segment size is related to maximum transfer unit (MTU), which is the size of the largest network layer protocol unit that can be communicated in a single network transaction. The maximum transfer unit includes the data segment and TCP and IP headers. To calculate an example, where the maximum transfer unit size in a TCP connection is 1500 bytes and a standard TCP header is 40 bytes, the maximum segment size is 1460 bytes. In some implementations, the maximum segment size in a wireless connection may be specified and agreed upon by the handshaking process between the source node and the destination node. A mismatch in the maximum segment size may occur where a received maximum segment size by a destination node is different than a specified maximum segment size provided by a source node. The specified maximum segment size may be the maximum segment size for a payload in the wireless communications protocol. The mismatch in the maximum segment size may be identified by any of the nodes in the network, including the electronic device, the remote database system, and the one or more gateway devices.

Figure 6:
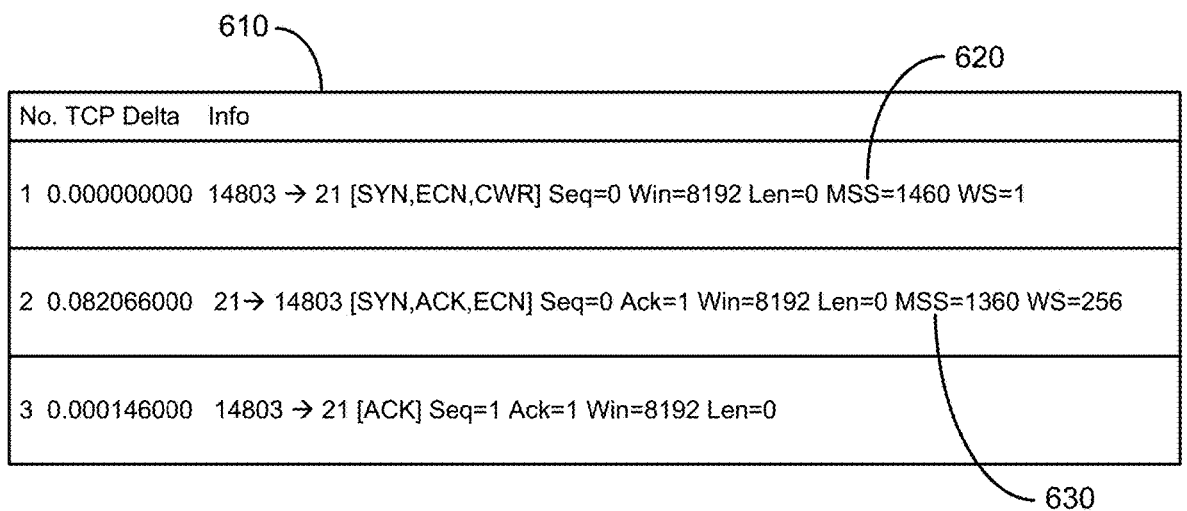
FIG. 6 illustrates an example network trace of packet transmissions between a source node and a destination node according to some implementations.

FIG. 6 illustrates an example network trace 610 of packet transmissions between a source node and a destination node according to some implementations. A network trace 610 in FIG. 6 shows a first packet having a source node as indicated by "14803" that is sent to a destination node as indicated by "21." The first packet includes a SYN flag and a payload set to a first maximum segment size 620 of 1460 bytes. The destination node sends a second packet back to the source node acknowledging receipt of the first packet. The second packet includes a SYN-ACK flag and a payload set to a second maximum segment size 630. The second maximum segment size 630 should be the same as the first maximum segment size 620.

However, an inconsistency between the second maximum segment size 630 sent with the SYN-ACK flag and the first maximum segment size 620 sent with the SYN flag is indicative of something wrong with the payload, which is indicative of a packet loss or message loss. Any one of the electronic device, the one or more gateway devices, and the remote database system may be configured to specify the maximum segment size and detect an inconsistency in a received maximum segment size in a confirmation acknowledgement.

Returning to the process 400 of FIG. 4, enabling a selective acknowledgement attribute between at least a source node and a destination node provides a mechanism for filtering data when there is a broken wireless connection. Broken wireless connections can be characterized by receipt of one or more duplicated acknowledgement packets at the destination node. A series of packets may be sent by the source node each with a sequence identification number. A series of response packets are sent by the destination node that acknowledges receipt of each of the sequence identification numbers. However, where any of the response packets are duplicated acknowledgement packets, this is indicative of a packet sent by the source node that was not received by the destination node. In other words, at least one of the packets was not delivered successfully. It will be understood that the source node and the destination node in the foregoing example may be used interchangeably.

Without selective acknowledgement enabled in the wireless connection between nodes, the node sending the duplicated acknowledgement packet will continue sending the duplicated acknowledgement packets until it confirms receipt of a packet with the appropriate sequence identification number (e.g., sequence identification numbers in order). However, this means that the other node does not send the packet with the appropriate sequence identification number until it receives the duplicated acknowledgement packet, and will resend all the packets following the packet with the appropriate sequence identification number even if they were successfully delivered in the first place. With selective acknowledgement enabled in the wireless connection between nodes, the node sending the duplicated acknowledgement packet will append sequence identification numbers of packets already received. When the other node sends the packet with the appropriate sequence identification number, it knows to not resend any packets that were already successfully delivered in the first place. Instead, it will only send the packet with the sequence identification number that was missing.

Figure 7A:
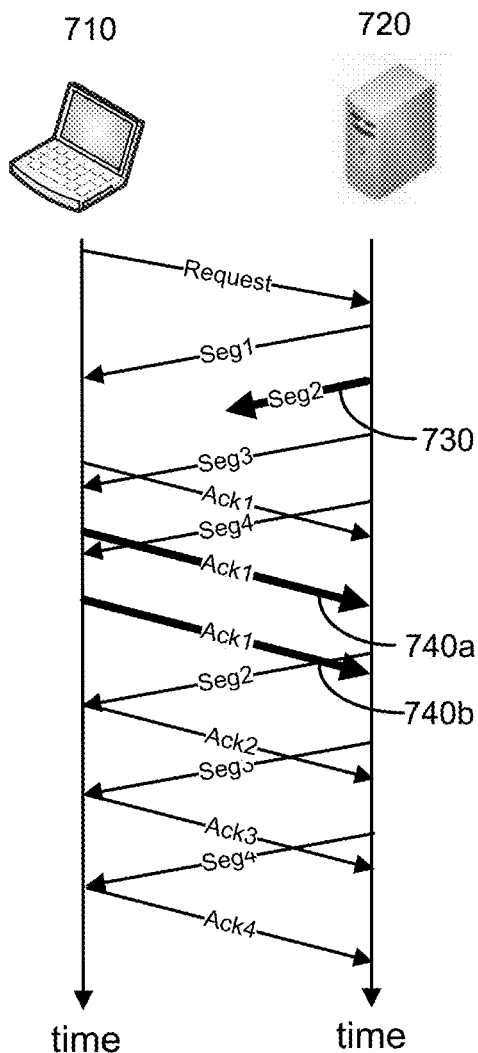
FIG. 7A illustrates a schematic diagram of an example wireless connection between a source node and a destination node without selective acknowledgement enabled.

FIG. 7A illustrates a schematic diagram of an example wireless connection between a source node 710 and a destination node 720 without selective acknowledgement enabled. A source node 710 sends a request, and the destination node 720 responds with four TCP segments or packets. The destination node 720 transmits all four packets to the source node 710, each of the packets having a sequence identification number labeled "Seg1," "Seg2," "Seg3," and "Seg4." A packet 730 labeled with the sequence identification number "Seg2" is lost or dropped and never reaches the source node 710. The source node 710 receives "Seg1" and acknowledges receipt of "Seg1," but then receives "Seg3" and "Seg4." Upon realizing that the sequence identification numbers are out of order, the source node 710 transmits duplicated acknowledgement packets 740a, 740b labeled "Ack1." This is to alert the destination node 720 that is has not received the packets in order and has only reliably received the packet labeled "Seg1" in order. Once the destination node 720 receives one of the duplicated acknowledgement packets 740a, 740b, the destination node 720 re-transmits the three remaining packets in order because the source node 710 only confirmed receipt of the packet labeled "Seg1." This means that the previously sent packets labeled "Seg3" and "Seg4" get discarded even when they arrived successfully in the first place.

Figure 7B:
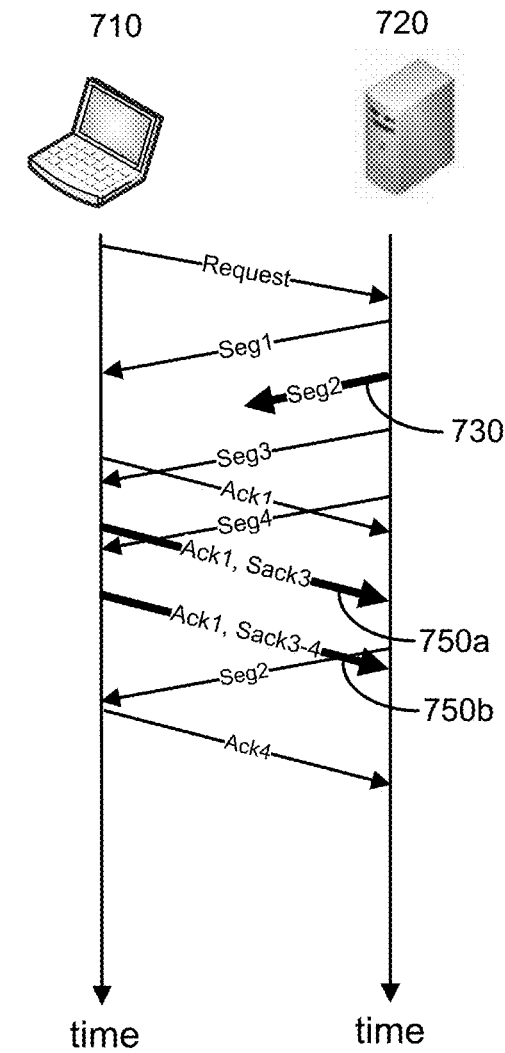
FIG. 7B illustrates a schematic diagram of an example wireless connection between a source node and a destination node with selective acknowledgement enabled according to some implementations.

FIG. 7B shows a schematic diagram of an example wireless connection between a source node 710 and a destination node 720 with selective acknowledgement enabled according to some implementations. As in FIG. 7A, the source node 710 sends a request, and the destination node 720 responds with four TCP segments or packets. The destination node 720 transmits all four packets to the source node 710, though the packet 730 labeled "Seg2" is lost or dropped. Upon realizing that the sequence identification numbers are out of order, the source node 710 transmits duplicated acknowledgement packets 750a, 750b. In contrast to FIG. 7A, information is appended to the duplicated acknowledgement packets 750a, 750b indicating what packets were already received successfully, so that a first duplicated acknowledgement packet 750a is appended with the label "Ack1, Sack3" and a second duplicated acknowledgement packet 750b is appended with the label "Ack1, Sack3-4." Once the destination node 720 receives the duplicated acknowledgement packets 750a, 750b, the destination node 720 re-transmits only the packet 730 that was not successfully received by the source node 710. The source node 710 sends an acknowledgement labeled "Ack4" indicating that is has received all four packets. This avoids buffering to re-transmit all messages from a sequence identification number that was not received. With selective acknowledgement enabled, not only can a data communication loss be identified but the data communication loss can be restored in an optimized manner. Any one of the electronic device, the one or more gateway devices, or the remote database system may be configured to synchronize sequence identification numbers in confirmation acknowledgement and detect receipt of an invalid sequence identification number to identify data communication loss. Furthermore, any one of the electronic device, the one or more gateway devices, and the remote database system may be configured to restore data communication loss by selective acknowledgement.

Returning to the process 400 of FIG. 4, a packet loss or message loss may be identified where there is a mismatch in a timestamp between at least a source node and a destination node. The timestamp may be provided in a field or option in a header of a packet. A timestamp may be recorded a time when a packet is transmitted and a timestamp may be recorded at a time when a packet is received, thereby allowing transit time to be calculated between the source node and the destination node. A mismatch in a timestamp between a source node and a destination node may be identified where a received timestamp received by a source/destination node is not greater than a previously provided timestamp from the source/destination node. The discrepancy in timestamps can be indicative that the packet received by the source/destination node is a duplicate packet or not in order. In other words, a difference in timestamps can be indicative of a failure of transmission of data, where the timestamp may indicate that previously transmitted data was already received and a source/destination node is expecting new data. In some implementations, the timestamps may be unified according to a reference time zone. That way, the time zones in which the electronic device, the one or more gateway devices, and the remote database system reside does not impact the differences in timestamps.

Figure 8:
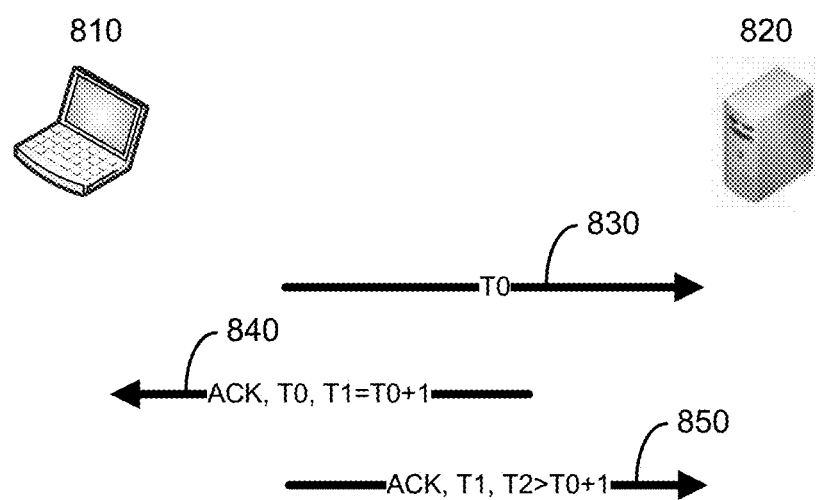
FIG. 8 illustrates a schematic diagram of packet transmissions sent between a source node and a destination node with timestamp fields according to some implementations.

FIG. 8 shows a schematic diagram of packet transmissions sent between a source node 810 and a destination node 820 with timestamp fields according to some implementations. A source node 810 can send a first packet 830 to a destination node 820 having an initial timestamp $T_0$. The destination node 820 can respond with a response packet 840 acknowledging the initial timestamp $T_0$ and confirming receipt of the first packet 830 at a response timestamp $T_1$. The response timestamp $T_1$ can also be represented by $T_0+1$, accounting for the transit time between the source node 810 and the destination node 820. The source node 810 can send an acknowledgement packet 850 that acknowledges the response timestamp $T_1$ and records an acknowledgement timestamp $T_2$ with the acknowledgement packet 850. If the acknowledgement timestamp $T_2$ received by the destination node 820 is greater than its response timestamp $T_1$ previously provided from the destination node 820, then the acknowledgement packet 850 is valid. If the acknowledgement timestamp $T_2$ received by the destination node 820 is less than or equal to its response timestamp $T_1$ previously provided from the destination node 820, then the acknowledgement packet 850 is invalid. To illustrate an example, if the destination node 820 says it last sent a message to the source node 810 yesterday at 1:00 pm PST, and the source node 810 sends a message to the destination node 820 providing its previously recorded timestamp of yesterday at 9:00 am PST, then the timestamp difference is indicative of data communication loss. It will be understood that the source node 810 and the destination node 820 may be used interchangeably with respect to timestamps and identifying data communication loss.

Returning to the process 400 in FIG. 4, at block 415, a notification is provided indicating the data communication loss. The notification may be provided from any of the nodes in the network, including the electronic device, the one or more gateway devices, and the remote database system. In some implementations, the notification may indicate where the data communication loss occurred so that an entity may be able to more efficiently restore the lost data, thereby restoring communication between nodes where wireless communication was broken or disrupted.

In some implementations, the electronic device may provide the notification through a feedback mechanism in the electronic device. For example, the electronic device may have a feedback component that provides the notification by a visual notification, audible notification, haptic notification, or combinations thereof. In some implementations, one or more gateway devices may provide the notification through a feedback mechanism in the one or more gateway devices, where the feedback mechanism can be a visual notification, audible notification, haptic notification, or combinations thereof. In some implementations, the one or more gateway devices may provide the notification using an accessible application layer, which can include providing the notification via email, text message, multimedia message, or mobile app message. In some implementations, the remote database system may provide the notification using an accessible application layer, which can include providing the notification via email, text message, multimedia message, or mobile app message.

Figure 9:
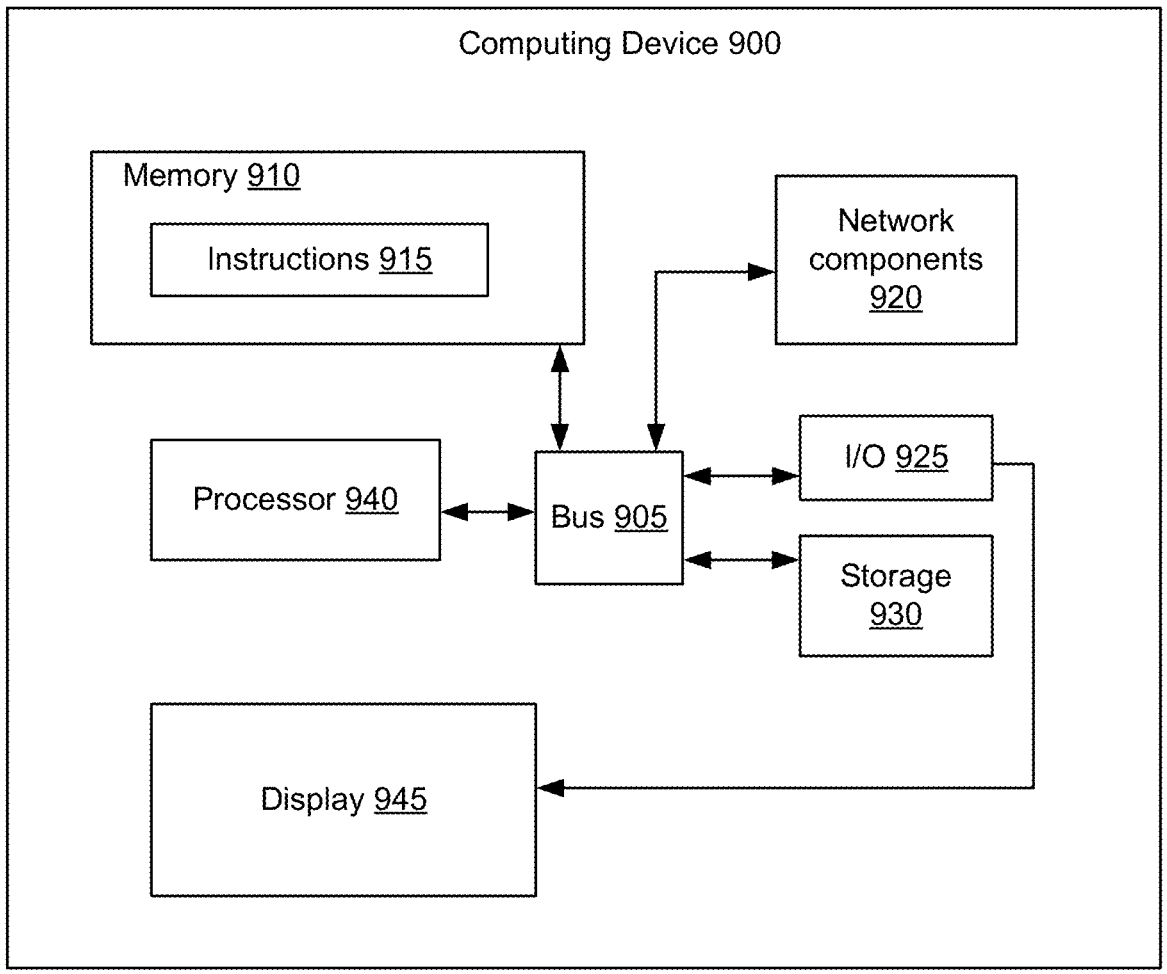
FIG. 9 illustrates an example computer system.

FIG. 9 illustrates a block diagram of an example computer system 900 usable for performing computing tasks. The computing device 900 may be, for example, electronic medical device 20, wireless gateway device 30, or remote database system 40. The computing device 900 can be or include, for example, a laptop computer, desktop computer, tablet, e-reader, smart phone or mobile device, smart watch, personal data assistant (PDA), or other electronic device.

The computing device 900 can include a processor 940 interfaced with other hardware via a bus 905. A memory 910, which can include any suitable tangible (and non-transitory) computer readable medium, such as RAM, ROM, EEPROM, or the like, can embody program components (e.g., instructions 915) that configure operation of the computing device 900. In some examples, the computing device 900 can include input/output ("I/O") interface components 925 (e.g., for interfacing with a display 945, keyboard, or mouse) and additional storage 930.

The computing device 900 can include network components 920. Network components 920 can represent one or more of any components that facilitate a network connection. In some examples, the network components 920 can facilitate a wireless connection and include wireless interfaces such as IEEE 802.11, Bluetooth, or radio interfaces for accessing cellular telephone networks (e.g., a transceiver/antenna for accessing CDMA, GSM, UMTS, or other mobile communications network). In other examples, the network components 920 can be wired and can include interfaces such as Ethernet, USB, or IEEE 1394.

Although FIG. 9 depicts a single computing device 900 with a single processor 940, the system can include any number of computing devices 900 and any number of processors 940. For example, multiple computing devices 900 or multiple processors 940 can be distributed over a wired or wireless network (e.g., a Wide Area Network, Local Area Network, or the Internet). The multiple computing devices 900 or multiple processors 940 can perform any of the steps of the present disclosure individually or in coordination with one another. Further, in some embodiments, a cloud computing system may be implemented for, for example, the remote database system 40.

The various illustrative logics, logical blocks, modules, circuits and algorithm steps described in connection with the implementations disclosed herein may be implemented as electronic hardware, computer software, or combinations of both. The interchangeability of hardware and software has been described generally, in terms of functionality, and illustrated in the various illustrative components, blocks, modules, circuits and steps described above. Whether such functionality is implemented in hardware or software depends upon the particular application and design constraints imposed on the overall system.

The hardware and data processing apparatus used to implement the various illustrative logics, logical blocks, modules and circuits described in connection with the aspects disclosed herein may be implemented or performed with a general purpose single- or multi-chip processor, a DSP, an ASIC, an FPGA or other programmable logic device, discrete gate or transistor logic, discrete hardware components, or any combination thereof designed to perform the functions described herein. A general purpose processor may be a microprocessor, or, any conventional processor, controller, microcontroller, or state machine. A processor also may be implemented as a combination of computing devices, such as a combination of a DSP and a microprocessor, a plurality of microprocessors, one or more microprocessors in conjunction with a DSP core, or any other such configuration. In some implementations, particular steps and methods may be performed by circuitry that is specific to a given function.

In one or more aspects, the functions described may be implemented in hardware, digital electronic circuitry, computer software, firmware, including the structures disclosed in this specification and their structural equivalents thereof, or in any combination thereof. Implementations of the subject matter described in this specification also can be implemented as one or more computer programs, i.e., one or more modules of computer program instructions, encoded on a computer storage media for execution by, or to control the operation of, data processing apparatus.

If implemented in software, the functions may be stored on or transmitted over as one or more instructions or code on a computer-readable medium. The steps of a method or algorithm disclosed herein may be implemented in a processor-executable software module which may reside on a computer-readable medium. Computer-readable media includes both computer storage media and communication media including any medium that can be enabled to transfer a computer program from one place to another. A storage media may be any available media that may be accessed by a computer. By way of example, and not limitation, such computer-readable media may include RAM, ROM, EEPROM, CD-ROM or other optical disk storage, magnetic disk storage or other magnetic storage devices, or any other medium that may be used to store desired program code in the form of instructions or data structures and that may be accessed by a computer. Also, any connection can be properly termed a computer-readable medium. Disk and disc, as used herein, includes compact disc (CD), laser disc, optical disc, digital versatile disc (DVD), floppy disk, and blu-ray disc where disks usually reproduce data magnetically, while discs reproduce data optically with lasers. Combinations of the above also may be included within the scope of computer-readable media. Additionally, the operations of a method or algorithm may reside as one or any combination or set of codes and instructions on a machine readable medium and computer-readable medium, which may be incorporated into a computer program product.

Various modifications to the implementations described in this disclosure may be readily apparent to those skilled in the art, and the generic principles defined herein may be applied to other implementations without departing from the spirit or scope of this disclosure. Thus, the claims are not intended to be limited to the implementations shown herein, but are to be accorded the widest scope consistent with this disclosure, the principles and the novel features disclosed herein.

Certain features that are described in this specification in the context of separate implementations also can be implemented in combination in a single implementation. Conversely, various features that are described in the context of a single implementation also can be implemented in multiple implementations separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. Further, the drawings may schematically depict one more example processes in the form of a flow diagram. However, other operations that are not depicted can be incorporated in the example processes that are schematically illustrated. For example, one or more additional operations can be performed before, after, simultaneously, or between any of the illustrated operations. Moreover, various ones of the described and illustrated operations can itself include and collectively refer to a number of sub-operations. For example, each of the operations described above can itself involve the execution of a process or algorithm. Furthermore, various ones of the described and illustrated operations can be combined or performed in parallel in some implementations. Similarly, the separation of various system components in the implementations described above should not be understood as requiring such separation in all implementations. As such, other implementations are within the scope of the following claims. In some cases, the actions recited in the claims can be performed in a different order and still achieve desirable results.

What is claimed is:
1. An electronic device, comprising:
a radio-frequency (RF) communications circuitry;
one or more sensors configured to measure and/or collect biometric data; and
a control system coupled to the RF communications circuitry, the control system configured to:
transmit the biometric data from the electronic device to a wireless gateway device in a first wireless connection, wherein the wireless gateway device is configured to upload the biometric data to a remote database system;

identify a data communication loss based at least on a mismatch of a confirmation acknowledgement attribute between two or more of: the electronic device, the wireless gateway device, or the remote database system, wherein the control system is configured to identify the data communication loss while a wireless connection is available and active between the two or more devices for which the data communication loss has occurred; and provide a notification indicating the data communication loss.

2. The electronic device of claim 1, wherein the control system is configured to identify the data communication loss while a wireless connection is available and active between the remote database system and the wireless gateway device.

3. The electronic device of claim 1, wherein the control system is configured to identify the data communication loss while the electronic device and the wireless gateway device are wirelessly paired.

4. The electronic device of claim 1, wherein the wireless gateway device is configured to upload the biometric data to the remote database system in a second wireless connection, the second wireless connection provided over a wireless local area network (WLAN) and the first wireless connection provided over a personal area network (PAN).

5. The electronic device of claim 1, further comprising:
a feedback component coupled to the control system, wherein the control system is configured to provide the notification through the feedback component by a visual notification, audible notification, haptic notification, or combinations thereof.

6. The electronic device of claim 1, wherein the wireless gateway device comprises an access point, wireless communications hub, mobile phone, smartphone, tablet, PDA, laptop computer, desktop computer, smart watch, or smart clothing.

7. The electronic device of claim 1, wherein the confirmation acknowledgement attribute includes a sequence identification number.

8. The electronic device of claim 7, wherein the control system configured to identify the data communication loss based at least on a mismatch of the sequence identification number is further configured to:
cause an initial sequence identification number in a SYN flag to be transmitted with the biometric data from a source node, wherein the source node comprises the electronic device or the wireless gateway device; and
determine a mismatch with the initial sequence identification number in an ACK flag transmitted from a destination node, wherein the destination node comprises the wireless gateway device or the remote database system.

9. The electronic device of claim 7, wherein the control system is further configured to:
cause an acknowledgement packet appended with an initial sequence identification number to be transmitted from a source node, wherein the source node includes the electronic device, the wireless gateway device, or the remote database system; and
cause a duplicated acknowledgement packet appended with the initial sequence identification number and one or more previously received sequence identification numbers to be transmitted from the source node.

10. The electronic device of claim 1, wherein the confirmation acknowledgement attribute includes a timestamp.

11. The electronic device of claim 10, wherein the control system configured to identify the data communication loss based at least on a mismatch of the timestamp is further configured to:
determine that a received timestamp received by a source/destination node is not greater than a previously provided timestamp from the source/destination node, wherein the source/destination node comprises the electronic device, the wireless gateway device, or the remote database system.

12. The electronic device of claim 1, wherein the confirmation acknowledgement attribute includes a maximum segment size.

13. The electronic device of claim 12, wherein the control system configured to identify the data communication loss based at least on a mismatch of the maximum segment size is further configured to:
determine that a received maximum segment size received by a destination node is different than a specified maximum segment size provided by a source node, wherein the source node comprises the electronic device or the wireless gateway device and the destination node comprises the wireless gateway device or the remote database system.

14. A gateway device comprising:
a radio-frequency (RF) communications circuitry; and
a control system coupled to the RF communications circuitry, the control system configured to:
connect the gateway device wirelessly with an electronic device configured to measure and/or collect biometric data;
receive the biometric data from the electronic device;
transmit the biometric data to one or more access points or a remote database system;
identify a data communication loss based at least on a mismatch of a confirmation acknowledgement attribute between two or more of: the electronic device, the gateway device, the one or more access points, or the remote database system, wherein the control system is configured to identify the data communication loss while a wireless connection is available and active between the two or more devices for which the data communication loss has occurred; and
provide a notification indicating the data communication loss.

15. The gateway device of claim 14, wherein the confirmation acknowledgement attribute is selected from a group consisting of: a sequence identification number, a timestamp, and a maximum segment size.

16. The gateway device of claim 14, wherein the control system configured to provide the notification indicating the data communication loss is configured to:
provide the notification via email, text message, multimedia message, or mobile app message.

17. A database system comprising:
a radio-frequency (RF) communications circuitry; and
a control system coupled to the RF communications circuitry, the control system configured to:
connect the database system wirelessly with a gateway device, wherein the gateway device is configured to receive biometric data measured and/or collected by an electronic device;
receive the biometric data from the gateway device;

identify a data communication loss based at least on a mismatch of a confirmation acknowledgement attribute between two or more of: the electronic device, the gateway device, one or more access points, or the database system, wherein the control system is configured to identify the data communication loss while a wireless connection is available and active between the two or more devices for which the data communication loss has occurred; and provide a notification indicating the data communication loss.

18. The database system of claim 17, wherein the confirmation acknowledgement attribute is selected from a group consisting of: a sequence identification number, a timestamp, and a maximum segment size.

19. The database system of claim 17, wherein the control system configured to provide the notification indicating the data communication loss is configured to:

provide the notification via email, text message, multimedia message, or mobile app message.

20. The database system of claim 17, wherein the control system is configured to identify the data communication loss while a wireless connection is available and active between the database system and the gateway device.

* * * * *